United States Patent [19]

Heaven et al.

[11] Patent Number: 5,318,528
[45] Date of Patent: Jun. 7, 1994

[54] STEERABLE SURGICAL DEVICES

[75] Inventors: Malcolm D. Heaven, Hopewell, N.J.; Robert C. Klapper, Sherman Oaks, Calif.

[73] Assignee: Advanced Surgical Inc., Princeton, N.J.

[21] Appl. No.: 45,681

[22] Filed: Apr. 13, 1993

[51] Int. Cl.⁵ .............................................. A61M 37/00
[52] U.S. Cl. ..................................... 604/95; 128/751; 606/205
[58] Field of Search .................. 604/95, 281; 606/205, 606/206; 128/751

[56] References Cited

U.S. PATENT DOCUMENTS

| | | | |
|---|---|---|---|
| 4,512,765 | 4/1985 | Muto | 604/281 |
| 4,581,017 | 4/1986 | Sahota | 606/192 |
| 4,807,626 | 2/1989 | McGirr | 604/95 |
| 4,935,017 | 6/1990 | Sylvanowicz | 604/281 |
| 4,945,920 | 8/1990 | Clossick | 606/205 |
| 5,069,226 | 12/1991 | Yamauchi et al. | 604/95 |

FOREIGN PATENT DOCUMENTS

| | | | |
|---|---|---|---|
| 2926339 | 1/1980 | Fed. Rep. of Germany | 604/95 |
| 3641935 | 6/1987 | Fed. Rep. of Germany | 606/205 |

*Primary Examiner*—John D. Yasko
*Assistant Examiner*—Anthony Gutowski
*Attorney, Agent, or Firm*—Burns, Doane, Swecker & Mathis

[57] ABSTRACT

A steerable surgical device including an inner tubular member and an outer tubular member surrounding the inner tubular member. A distal end of the inner tubular member and/or the outer tubular member is prebent in a curved configuration. A distal end of the device can be oriented in a desired direction by rotating the inner and outer tubular members with respect to each other. A tool such as an arthroscopic grasper can be mounted on a distal end of the inner and/or outer tubular members and the tool can be oriented in any desired direction simply by rotating one of the tubular members with respect to the other tubular member.

19 Claims, 1 Drawing Sheet

STEERABLE SURGICAL DEVICES

BACKGROUND OF THE INVENTION

1. Field of the Invention

The invention relates to an articulating device and method of using. In addition, the invention relates to the use of the articulating device for steering medical devices such as the distal portion of medical devices typically used in minimally invasive surgery.

2. Description of Related Art

Rigid instruments, which may, for example, be catheters, graspers, or other tools, limit the ability of the surgeon to access the interior portions of the body. By having articulateable distal portions this adds an extra degree of freedom, thus reducing the need for changing tools during a procedure, and as a result reducing the time needed for the procedure to the mutual benefit of surgeon and patient alike.

As already stated the majority of tools used in these procedures are rigid. There are a variety of devices which have a degree of steerability added via a fixed curve being introduced in the distal end, and some devices which have steerable tips. Examples of steerable tips can be found in commonly owned and copending application Ser. No. 07/903,587 and U.S. Pat. No. 4,934,340 ("Wendel"), and U.S. Pat. No. 5,114,403 ("Clarke"). In many of these devices the distal tip, on being articulated, suffers from the problem of not being able to sustain any appreciable end loading, and hence buckles easily. It is also extremely desirable for the devices to be hollow, or in the form of a cannula, such that any debris generated during a procedure may be aspirated from the operation site without the need for extra equipment. Thus, there is a need in the art for small diameter devices which freely articulate, are capable of resisting substantial end-loading, and due to their tubular nature enable simultaneous removal of debris via fluid flow.

Various devices are known for steering medical devices such as catheters. For instance, steering mechanisms are discussed in WO92/14506 ("Middleman") and U.S. Pat. Nos. 4,353,358 ("Emerson"); 3,470,876 ("Barchilon") and 4,245,624 ("Komiya").

Middleman discloses a device for insertion into a body, the device including an elongated tube or cannula, an elastic member for bending the cannula and a straightener preventing the elastic member from bending the cannula. The straightener and elastic member are capable of relative axial movement so that the straightener can be positioned to prevent or allow the elastic member to bend the cannula. The elastic member can be formed from a superelastic shape memory alloy. In another embodiment of the device, two elastic members are housed in parallel lumens of a cannula. The portions of the elastic members which are housed within the distal segment of the cannula are curved and can be positioned within the lumens such that they tend to curve in opposite directions. The elastic members can be identically curved and of the same elastic material such as a superelastic shape-memory alloy whereby each applies a force opposite to the other so that the net effect is that the distal segment is straight. The lumens permit rotation of the elastic members therein and the elastic members can be rotated together, or in unison, to bend the distal segment. In this case, a stiffener is not needed so that the cannula can remain flexible.

Emerson discloses a disposable sigmoidoscope having a tubular portion of plastic material wherein a free end is weakened by providing one or more cut-outs or notches or by making the side of the tubular portion thinner. An operator cord member of wire, plastic or string member is attached to the free end and extends along the outer surface of the segments between the cut-outs, on the inside of the segments or through the weakened side of the device. Pulling on the member allows the tubular member to be bent somewhat but not so much that the operator can no longer see through the passage through the tubular member. A protective outer layer or sheath covers the cut-outs in order to prevent discomfort to the patient during insertion and withdrawal of the device and prevent material from entering the device through the cut-outs.

Barchilon discloses a ⅛ to 2 inch diameter catheter including an outer tube, an inner tube and a rigid end piece connecting the distal ends of the inner and outer tubes. The end piece has a flange and four tensioning cords are attached thereto such that each cord is offset 90° with respect to each other. The inner and outer tubes are of flexible material such as a silicone compound having a durometer of 48. The cords are of material such as wire or nylon and the catheter can be bent in any desired direction by pulling on one or more of the cords.

Komiya discloses an endoscope having an observation optical system, a flexible plastic guide tube and a wire, each of which is located in a respective one of three channels extending longitudinally through a distal end of the endoscope. The guide tube is movable longitudinally beyond the distal end of the endoscope and the wire is attached to a distal end of the guide tube for bending the guide tube. When the guide tube is empty, liquid can be sprayed from or sucked into the distal end thereof. On the other hand, a medical implement such as forceps can be inserted into the guide tube and the wire can be used to bend the guide tube and medical implement toward a prescribed location in a body cavity. The guide tube can be made more flexible by using a plastic material foamed at a progressively higher rate at the distal end thereof. Alternatively, the guide tube can be made thinner at the distal end thereof or the guide tube can be surrounded by a coil of plastic or metal which has a progressively larger pitch toward the distal end of the guide tube.

It would be desirable in the medical field to have a steering device which provides resistance to end-loading while permitting a wide range of movement of a distal end of a medical device.

SUMMARY OF THE INVENTION

The invention provides a steerable surgical device comprising an inner tubular member and an outer tubular member surrounding the inner tubular member. A distal end of at least one of the inner and outer tubular members is prebent in a curved configuration and the inner and outer tubular members are rotatable with respect to each other so that a distal end of the device can be oriented in a desired direction by rotating the tubular members with respect to each other.

According to one embodiment, a proximal end of the inner tubular member extends beyond a proximal end of the outer tubular member and the device is steered by rotating the outer tubular member while preventing the inner tubular member from rotating. The inner and/or outer tubular member can be prebent in a non-linear configuration such as an arcuate configuration. At least one of the inner and outer tubular members can be of a polymer material or of a nickel-titanium shape memory alloy. Also, the outer tubular member and the inner tubular member can be of the same material or different materials.

The inner and/or outer tubular member can support a surgical tool which extends beyond the distal end of the inner tubular member. For instance, the tool can comprise an arthroscopic grasper. The grasper can include a pair of jaws and a jaw activation wire, the jaws being supported on an end of the inner tubular member. A flexible joint cover can extend between the inner tubular member and the jaws, the joint cover providing a seal between an outer periphery of the jaws and an outer periphery of the inner tubular member. The jaws can be hinged together at one end thereof and the activation wire can be attached to one of the jaws. The device can further include an aspirating device in fluid communication with a proximal end of the inner tubular member, the inner tubular member including a passage therein through which debris can be removed from an operation site by actuating the aspirating device.

The invention also provides a method of steering the surgical device described above. The method includes placing a distal end of the device at a site within a body of a patient and steering the distal end of the device by rotating one tubular member with respect to the other tubular member. When the device includes a surgical tool at the distal end of the device, the method can further include manipulating the tool during or subsequent to the steering step. For instance, the tool can comprise the arthroscopic grasper described above and the method can include removing debris from the site by activating the aspirating device so that debris is sucked into the distal end of the passage and passes outwardly of the proximal end of the passage. The distal end of the device can be deformed from a straightened configuration to a curved configuration by rotating the inner and outer tubular members with respect to each other during the steering step.

DETAILED DESCRIPTION OF THE INVENTION

Figure 1:
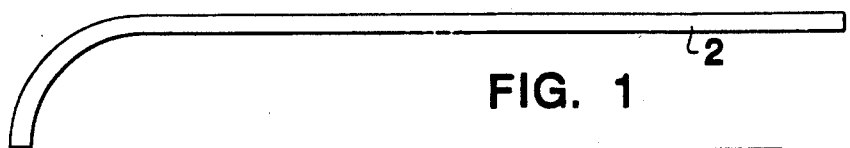
FIG. 1 shows an inner tubular member of the surgical device according to the invention.

The surgical device according to the invention offers considerable improvement over existing surgical instruments. In particular, the steerable surgical device according to the invention can provide substantial resistance to end-loading and a range of movement of the distal tip of the device which makes it possible to reach and manipulate tissue structures in relatively inaccessible areas of the body. This provides a great advantage over existing methods wherein it is necessary to withdraw the instrument and replace it with another instrument having a different working angle.

The device according to the invention includes two coaxial tubes having an adjustable curved section at a distal portion thereof. The tubes are rotatable with respect to each other and the degree of curvature of the distal portion of the device can be adjusted depending on the extend of rotation of one of the tubes relative to the other. The degree of curvature and resistance to end loading will depend on factors such as choice of materials of construction and the respective wall thickness of the two tubes.

The two concentric tubes can be of the same or different materials such as beryllium-copper alloys, pseudoelastic nickel-titanium alloys or any other high strength material such as engineering polymers which have a suitable flexural modulus and which can accept the range of deflection needed without exceeding their inherent yield point. In addition, the distal portions of the two tubes can be prebent with the same degree of curvature, different degrees of curvature or one of the tubes can be prebent and the other tube can have a straight (i.e. linear) configuration. However, once assembled such that the two tubes are concentric with each other, rotation of the tubes relative to each other should allow the angulation of the distal tip of the device to be changed upon rotation of the tubes relative to each other.

The passage in the device can be used to accommodate or house a medical implement, such as a light source, forceps, catheter, graspers for arthroscopic procedures, scissors or other devices used, for example, in laparoscopic procedures. In use, the device can be introduced into a body cavity by any conventional surgical procedure. Also, an operator cord member composed of metallic, plastic or cellulosic materials, can be attached to a portion of the implement for actuation thereof. Preferably, the operator member is composed of metal, such as a wire. However, the operator cord may also include combinations of the above-mentioned materials, such as a wire coated with plastic or polymeric materials.

Upon rotation of the tubular members with respect to each other, the distal end of the device can be steered to more easily follow the shape of the body cavity into which the device is inserted or perform work such as removing tissue with a medical tool associated with the device. Since many body cavities are serpentine in shape, it is highly desirable to be able to guide the medical steering device around corners as easily as possible, and this is greatly facilitated by the ability of the distal end of the device to be able to be bent under control of the operator during insertion.

The device can be provided with a protective outer member or sheath which extends between the outer tubular member and the tool. The sheath reduces resistance to movement which might be caused by exposed edges of the outer tubular member and the tool and/or possible discomfort to the patient during insertion and withdrawal of the device. The sheath also prevents materials from entering the side of the device through the gap between the tool and the tubular members which could adversely affect the operation of a medical implement mounted in or on the tubular members. The sheath may be constructed of various materials which are suitable for this application. Preferably the sheath is composed of a plastic material. Additionally, the sheath may extend the entire length of the outer tubular member. If desired, the sheath can also be used to cover any control wire or wires used to activate the tool and thus prevent contact of the control wire with the patient.

Figure 2:
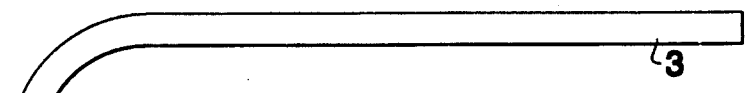
FIG. 2 shows an outer tubular member of the surgical device according to the invention.
Figure 3:
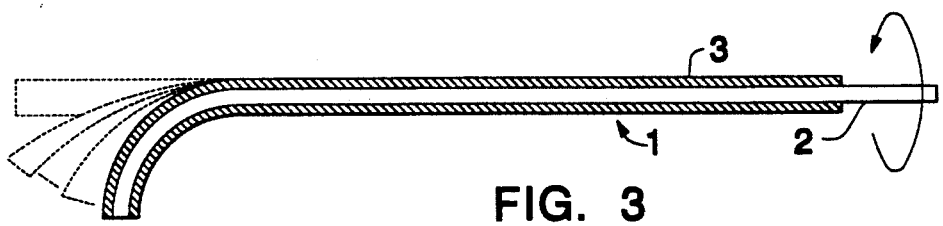
FIG. 3 shows an assembly of the tubular members shown in FIGS. 1 and 2.

The surgical steering device according to the invention will now be described with reference to FIGS. 1-6. In particular, the surgical steering device 1 includes an inner tubular member 2 and an outer tubular member 3. As shown in FIG. 1, the inner tubular member 2 can be prebent at the distal end thereof. As shown in FIG. 2, the outer tubular member 3 can be prebent in a curved configuration at the distal end thereof. As shown in FIG. 3, the inner and outer tubular members are assembled so as to be concentric with each other. Thus, the outer tubular member 2 can be rotated to change the angle of the distal end of the device 1 such that the distal end can be deformed between a bent configuration having approximately a 90° bend to a straight configuration and configurations therebetween, as shown by the dotted lines in FIG. 3.

Figure 6:
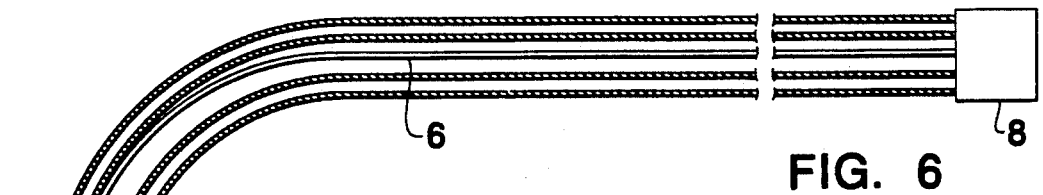
FIG. 6 shows the assembly of FIG. 4 with the outer tubular member of FIG. 2 surrounding the inner tubular member.

Many different medical implements may be inserted into or mounted on the device 1, such as optical devices, catheterization devices, tissue removal devices, cutting devices and other various surgical and diagnostic devices. The usefulness of the invention may be best described via a preferred embodiment such as, but not limited to, an arthroscopic grasper 4, as shown in FIGS. 4-6.

Figure 4:
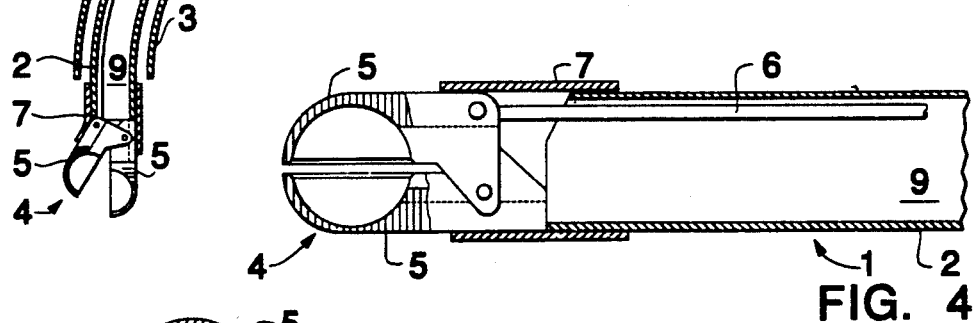
FIG. 4 shows a surgical tool mounted on a distal end of the inner tubular member shown in FIG. 1.
Figure 5:
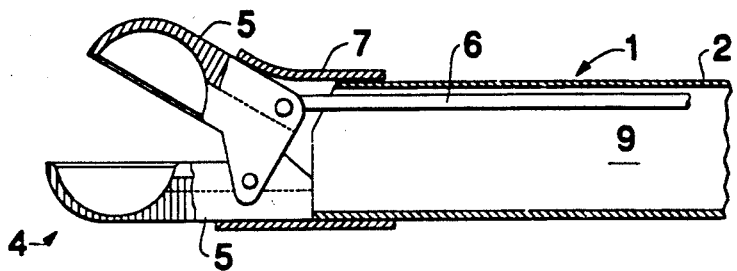
FIG. 5 shows how the tool of FIG. 4 is activated.

As shown in FIG. 4, the tool 4 is mounted on a distal end of the inenr tubular member 2. The tool 4, which is this case is an anthroscopic grasper, includes a pair of jaws 5 and a flexible joint cover 7 extends between the jaws 5 and the inner tubular member 2. The joint cover 7 provides a seal between the outer periphery of the jaws 5 and the outer periphery of the inner tubular member 2. The jaws 5 are hinged together at one end thereof and an activation wire 6 is attached to one of the jaws 5. As shown in FIG. 5, when tension is applied to the activation wire 6, the jaws 5 are opened by pivoting one jaw away from the other one of the jaws 5. As shown in FIG. 6, the inner tubular member 2 can be mounted within the outer tubular member 3 to allow steering of the tool 4 upon rotation of the tubular members 2, 3 with respect to each other. Further, an aspirating device 8 can be connected to a proximal end of the inner tubular member 2 whereby debris can be removed from a site within a body of a patient by sucking the debris into a distal end of a passage 9 in the inner tubular member 2.

Thus, there has been shown and described an improved medical steering device which fulfills all of the objects and advantages sought therefor. It will become apparent to those skilled in the art, however, that many changes, modifications, alterations, and other uses and applications of the subject device are possible, and all such changes, modifications, alterations, and other uses and applications that do not depart from the spirit and scope of the invention are deemed to be covered by invention.

What is claimed is:

1. A steerable medical device comprising:
an inner tubular member and an outer tubular member surrounding the inner tubular member, at least one of the inner and outer tubular members being prebent in a curved configuration at the distal end and the inner and outer tubular members being rotatable with respect to each other so that the distal end of the device can be oriented in a desired direction by rotating the inner tubular member with respect to the outer tubular member, the distal end of the device being deformed from a straightened configuration to a curved configuration by rotating the inner and outer tubular members with respect to each other.

2. The device of claim 1, wherein a proximal end of the inner tubular member extends beyond a proximal end of the outer tubular member and the device is steered by rotating the outer tubular member while preventing the inner tubular member from rotating.

3. The device of claim 1, wherein the inner tubular member is prebent is an arcuate configuration and the outer tubular member is prebent in an arcuate configuration.

4. The device of claim 1, wherein the inner tubular member includes a tool which extends beyond a distal end of the outer tubular member.

5. The device of claim 1, wherein at least one of the inner and outer tubular members is of a nickel-titanium shape memory alloy.

6. The device of claim 1, wherein the outer tubular member and the inner tubular member is of the same material.

7. The device of claim 1, wherein at least one of the inner and outer tubular members is of a polymer material.

8. A steerable surgical device comprising:
an inner tubular member and an outer tubular member surrounding the inner tubular member, a distal end of at least one of the inner and outer tubular members being prebent in a curved configuration and the inner and outer tubular members being rotatable with respect to each other so that a distal end of the device can be oriented in a desired direction by rotating the inner tubular member with respect to the outer tubular member, the inner tubular member including a tool which extends beyond a distal end of the outer tubular member, the tool comprising an arthroscopic grasper.

9. The device of claim 8, wherein the grasper includes a pair of jaws and a jaw activation wire, the jaws being supported on the distal end of the inner tubular member.

10. The device of claim 9, wherein a flexible joint cover extends between the inner tubular member and the jaws, the joint cover providing a seal between an outer periphery of the jaws and an outer periphery of the inner tubular member.

11. The device of claim 10, wherein the jaws are hinged together at one end thereof and the activation wire is attached to one of the jaws.

12. The device of claim 8, further comprising an aspirating device in fluid communication with a proximal end of the inner tubular member, the inner tubular member including a passage therein through which debris can be removed from an operation site by actuating the aspirating device.

13. A method of steering a medical device wherein the device includes an inner tubular member, an outer tubular member surrounding the inner tubular member and a distal end of at least one of the inner and outer tubular members is prebent in a curved configuration, the method comprising steps of:
placing a distal end of the device at a site within a body of a patient; and
steering the distal end of the device by rotating the inner tubular member with respect to the outer tubular member, the distal end of the device being deformed from a straightened configuration to a curved configuration by rotating the inner and outer tubular members with respect to each other during the steering step.

14. The method of claim 13, wherein the device includes a tool at the distal end of the device, the method further including manipulating the tool during or subsequent to the steering step.

15. The method of claim 14, wherein the tool comprises an arthroscopic grasper having a pair of jaws and a jaw activation wire, the jaws being opened and closed during the manipulating step.

16. The method of claim 15, wherein the inner tubular member includes a passage extending from the distal end of the device to a proximal end of the device and an aspirating device is connected to the proximal end of the inner tubular member, the method further including removing debris from the site by activating the aspirating device so that debris is sucked into the distal end of the passage and the debris passes outwardly of the proximal end of the passage.

17. The method of claim 13, wherein the inner and outer tubular members each have a prebent configuration and an outer periphery of the inner tubular member is in contact with an inner periphery of the outer tubular member, the distal end of the device being straightened during the steering step by rotating the members until the prebent configuration of the inner tubular member cancels the prebent configuration of the outer tubular member.

18. The method of claim 13, wherein the inner tubular member is prevented from rotating during the steering step.

19. The method of claim 13, wherein a distal end of the inner tubular member extends beyond the distal end of the outer tubular member and a tool is mounted at the distal end of the inner tubular member, the method further including manipulating tissue structures at the site during the steering step.

* * * * *